US011402312B2

(12) United States Patent
Beaupre

(10) Patent No.: US 11,402,312 B2
(45) Date of Patent: Aug. 2, 2022

(54) METHODS AND SYSTEMS FOR HANDLING FRESH CONCRETE BASED ON HYDRAULIC PRESSURE AND ON RHEOLOGICAL PROBE PRESSURE

(71) Applicant: COMMAND ALKON INCORPORATED, Birmingham, AL (US)

(72) Inventor: Denis Beaupre, Québec (CA)

(73) Assignee: COMMAND ALKON INCORPORATED, Birmingham, AL (US)

( * ) Notice: Subject to any disclaimer, the term of this patent is extended or adjusted under 35 U.S.C. 154(b) by 0 days.

(21) Appl. No.: 16/968,213

(22) PCT Filed: Feb. 7, 2019

(86) PCT No.: PCT/US2019/017036
§ 371 (c)(1),
(2) Date: Aug. 7, 2020

(87) PCT Pub. No.: WO2019/157172
PCT Pub. Date: Aug. 15, 2019

(65) Prior Publication Data
US 2021/0055195 A1   Feb. 25, 2021

Related U.S. Application Data

(60) Provisional application No. 62/627,880, filed on Feb. 8, 2018.

(51) Int. Cl.
*G01N 11/14*   (2006.01)
*B60P 3/16*   (2006.01)
(Continued)

(52) U.S. Cl.
CPC ........... *G01N 11/14* (2013.01); *B60P 3/16* (2013.01); *G01N 33/383* (2013.01); *G01N 2011/0006* (2013.01); *G01N 2011/0053* (2013.01)

(58) Field of Classification Search
CPC ......... B01F 15/00162; B01F 15/00188; B01F 15/00201; B01F 15/00246; G01N 33/383;
(Continued)

(56) References Cited

U.S. PATENT DOCUMENTS 2,630,706 A * 3/1953 Maxon, Jr. ............ G01N 11/10
73/54.03
3,069,900 A * 12/1962 Kimberly ............... G01N 11/14
73/54.32
(Continued)

FOREIGN PATENT DOCUMENTS

AU   2012203925 A1   7/2012
CA      2885383 A1   3/2014
(Continued)

*Primary Examiner* — David A. Rogers
(74) *Attorney, Agent, or Firm* — Rothwell, Figg, Ernst & Manbeck, P.C.

(57) ABSTRACT

There are described methods and systems for handling fresh concrete inside a drum. In an aspect, a method of determining calibration data for use in determining workability of fresh concrete inside a rotating drum based on hydraulic pressure is described. This method has receiving a probe pressure value indicative of pressure exerted on a rheological probe mounted inside the drum and immerged in the fresh concrete; determining a workability value indicative of workability of the fresh concrete based on the probe pressure value and on calibration data for the rheological probe; receiving a hydraulic pressure value indicative of pressure of a hydraulic fluid used for rotating the drum; and determining
(Continued)

hydraulic calibration data by associating the hydraulic pressure value and the workability value to one another.

20 Claims, 14 Drawing Sheets

(51) Int. Cl.
  *G01N 33/38* (2006.01)
  *G01N 11/00* (2006.01)
(58) Field of Classification Search
  CPC .......... G01N 2011/0046; G01N 11/10; G01N 11/00; G01N 9/36; G01N 2011/006; G01N 33/38
  See application file for complete search history.

(56) References Cited

U.S. PATENT DOCUMENTS

| | | | | |
|---|---|---|---|---|
| 3,688,588 | A * | 9/1972 | Hill | G01N 9/10 |
| | | | | 73/451 |
| 4,193,291 | A * | 3/1980 | Lynnworth | G01F 1/20 |
| | | | | 376/245 |
| 4,356,723 | A * | 11/1982 | Fay | G01N 11/00 |
| | | | | 73/54.03 |
| 4,900,154 | A * | 2/1990 | Waitzinger | G01N 33/383 |
| | | | | 366/56 |
| 4,915,297 | A * | 4/1990 | Norman | B28C 7/003 |
| | | | | 122/20 A |
| 4,981,042 | A * | 1/1991 | Reeves | G01N 9/16 |
| | | | | 73/454 |
| 5,086,646 | A * | 2/1992 | Jamison | G01N 9/00 |
| | | | | 73/65.01 |
| 5,541,855 | A * | 7/1996 | Enzler | G01N 11/14 |
| | | | | 366/142 |
| 5,695,280 | A * | 12/1997 | Baker | B28C 7/0007 |
| | | | | 366/17 |
| 5,948,970 | A * | 9/1999 | Te'eni | B28B 23/0031 |
| | | | | 73/54.03 |
| 6,227,039 | B1 * | 5/2001 | Te'eni | C04B 40/0032 |
| | | | | 73/54.03 |
| 6,918,292 | B2 * | 7/2005 | Go Boncan | G01N 33/383 |
| | | | | 73/149 |
| 6,957,586 | B2 * | 10/2005 | Sprague | G01F 1/3209 |
| | | | | 73/204.21 |
| 7,384,180 | B2 * | 6/2008 | Jarvinen | G01N 33/383 |
| | | | | 366/2 |
| D638,729 | S * | 5/2011 | Beaupre | D10/78 |
| 8,020,431 | B2 * | 9/2011 | Cooley | B28C 5/422 |
| | | | | 73/54.03 |
| 8,118,473 | B2 * | 2/2012 | Compton | B28C 5/422 |
| | | | | 366/17 |
| 8,818,561 | B2 * | 8/2014 | Koehler | G01N 11/00 |
| | | | | 700/265 |
| 9,199,391 | B2 * | 12/2015 | Beaupre | B28C 7/024 |
| 9,511,510 | B2 * | 12/2016 | Roy | G01N 11/14 |
| 9,550,312 | B2 * | 1/2017 | Roberts | G01N 33/383 |
| 9,702,863 | B2 * | 7/2017 | Beaupre | B28C 5/422 |
| 10,052,794 | B2 * | 8/2018 | Beaupre | B28C 7/12 |
| 10,126,288 | B2 * | 11/2018 | Radjy | G01N 33/383 |
| 10,183,418 | B2 * | 1/2019 | Jordan | G01N 33/383 |
| 10,363,684 | B2 * | 7/2019 | Roberts | G01N 11/00 |
| 10,429,285 | B2 * | 10/2019 | Uusivirta | G01N 11/14 |
| 10,520,410 | B2 * | 12/2019 | Beaupre | G01N 11/10 |
| 10,527,534 | B2 * | 1/2020 | McAnally | G01N 11/16 |
| 11,041,794 | B2 * | 6/2021 | Beaupre | G01N 11/00 |
| 2005/0087002 | A1 * | 4/2005 | Kanzaki | G01N 11/162 |
| | | | | 73/54.28 |
| 2007/0023551 | A1 * | 2/2007 | Aichinger | B28C 7/0413 |
| | | | | 241/34 |
| 2007/0295104 | A1 * | 12/2007 | Ellegood | G01F 23/68 |
| | | | | 73/861.79 |
| 2009/0037026 | A1 * | 2/2009 | Sostaric | B01F 15/00207 |
| | | | | 700/265 |
| 2010/0161457 | A1 | 6/2010 | Katz et al. | |
| 2011/0004332 | A1 * | 1/2011 | Andersen | C04B 40/0032 |
| | | | | 700/103 |
| 2011/0077778 | A1 * | 3/2011 | Berman | G05B 15/02 |
| | | | | 700/265 |
| 2012/0020180 | A1 | 1/2012 | Koehler et al. | |
| 2012/0186341 | A1 * | 7/2012 | Oike | G01F 23/363 |
| | | | | 73/317 |
| 2012/0204625 | A1 | 8/2012 | Beaupre et al. | |
| 2012/0250446 | A1 | 10/2012 | Cook et al. | |
| 2013/0238255 | A1 | 9/2013 | Cooley et al. | |
| 2014/0044477 | A1 | 2/2014 | Stanley | |
| 2014/0104066 | A1 | 4/2014 | Jordan et al. | |
| 2014/0104972 | A1 | 4/2014 | Roberts et al. | |
| 2015/0078417 | A1 * | 3/2015 | Verdino | G01K 1/024 |
| | | | | 374/142 |
| 2015/0336290 | A1 | 11/2015 | Roy et al. | |
| 2015/0355160 | A1 * | 12/2015 | Berman | G01N 11/14 |
| | | | | 73/54.03 |
| 2015/0356688 | A1 | 12/2015 | Katz et al. | |
| 2016/0025700 | A1 * | 1/2016 | Beaupre | B28C 7/02 |
| | | | | 73/433 |
| 2017/0028586 | A1 | 2/2017 | Jordan et al. | |
| 2017/0108421 | A1 * | 4/2017 | Beaupre | G01N 11/10 |
| 2017/0217047 | A1 * | 8/2017 | Leon | B28C 5/4231 |
| 2018/0100791 | A9 * | 4/2018 | Beaupre et al. | G01N 11/14 |
| 2018/0319040 | A1 * | 11/2018 | Beaupre | B28C 7/0418 |
| 2020/0078987 | A1 * | 3/2020 | Beaupre | G01N 11/14 |
| 2020/0225258 | A1 * | 7/2020 | Beaupre | G01P 3/48 |
| 2020/0232966 | A1 * | 7/2020 | Beaupre | G01N 9/16 |
| 2020/0282597 | A1 * | 9/2020 | Beaupre | C04B 40/0028 |
| 2021/0001765 | A1 * | 1/2021 | Beaupre | B28C 5/422 |
| 2021/0031407 | A1 * | 2/2021 | Roberts | B28C 5/4231 |
| 2021/0031408 | A1 * | 2/2021 | Beaupre | B28C 5/422 |
| 2021/0055195 | A1 * | 2/2021 | Beaupre | B28C 7/024 |
| 2021/0178632 | A1 * | 6/2021 | Bollin | B28C 7/026 |
| 2021/0187786 | A1 * | 6/2021 | Beaupre | B28C 5/422 |

FOREIGN PATENT DOCUMENTS

| | | | | |
|---|---|---|---|---|
| CA | | 2930468 A1 | 5/2015 | |
| CA | | 2945663 A1 | 10/2015 | |
| CA | | 2866958 C | 6/2016 | |
| CA | | 2917536 C | 8/2018 | |
| DE | | 2552707 A * | 5/1977 | |
| WO | WO-2005029045 A1 * | | 3/2005 | ............ G01N 11/14 |
| WO | WO-2007060272 A3 * | | 7/2007 | ........ B01F 15/00207 |
| WO | | 2008/042252 A3 | 4/2008 | |
| WO | | 2010/110814 A1 | 9/2010 | |
| WO | | 2010/111204 A1 | 9/2010 | |
| WO | | 2011162878 A1 | 12/2011 | |
| WO | | 2016/023119 A1 | 2/2016 | |
| WO | | 2016/196599 A1 | 12/2016 | |
| WO | | 2017/099711 A1 | 6/2017 | |
| WO | | 2017/180625 A1 | 10/2017 | |

* cited by examiner

| Ppi (kPa) | ROTATION SPEED Vr1 | | | | | | |
|---|---|---|---|---|---|---|---|
| | VOLUME VALUE Vi (m³) | | | | | | |
| W (cm) | V1 | V2 | V3 | V4 | V5 | V6 | |
| W1 | Ph1 | Ph8 | - | - | - | - | |
| W2 | Ph2 | Ph9 | - | - | - | - | |
| W3 | Ph3 | - | - | - | - | - | |
| W4 | Ph4 | - | - | - | - | - | |
| W5 | Ph5 | - | - | - | - | - | |
| W6 | Ph6 | - | - | - | - | - | |
| W7 | Ph7 | - | - | - | - | - | |

Fig. 9A

| Ppi (kPa) | ROTATION SPEED Vr2 | | | | | | |
|---|---|---|---|---|---|---|---|
| | VOLUME VALUE Vi (m³) | | | | | | |
| W (cm) | V1 | V2 | V3 | V4 | V5 | V6 | |
| W1 | Ph1 | Ph8 | - | - | - | - | |
| W2 | Ph2 | Ph9 | - | - | - | - | |
| W3 | Ph3 | - | - | - | - | - | |
| W4 | Ph4 | - | - | - | - | - | |
| W5 | Ph5 | - | - | - | - | - | |
| W6 | Ph6 | - | - | - | - | - | |
| W7 | Ph7 | - | - | - | - | - | |

Fig. 9B

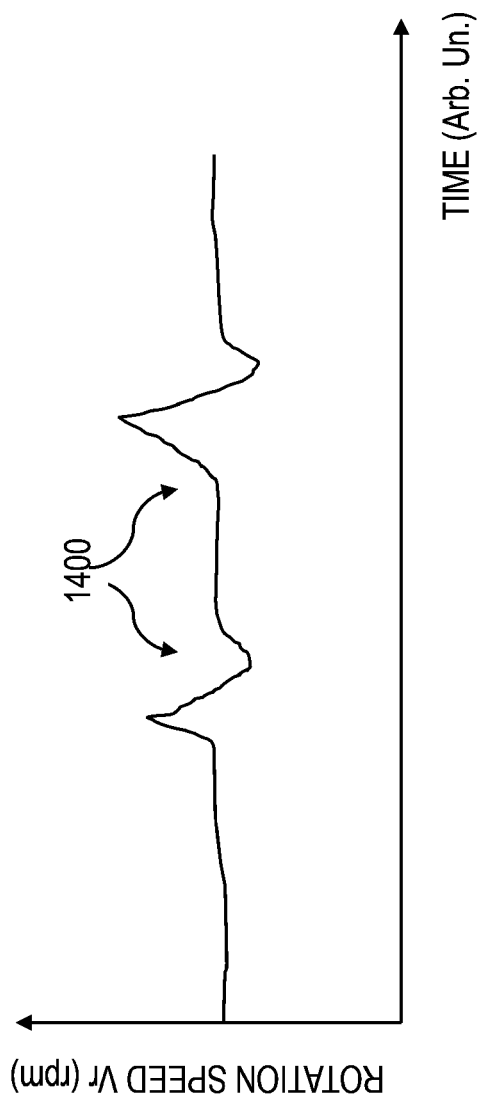
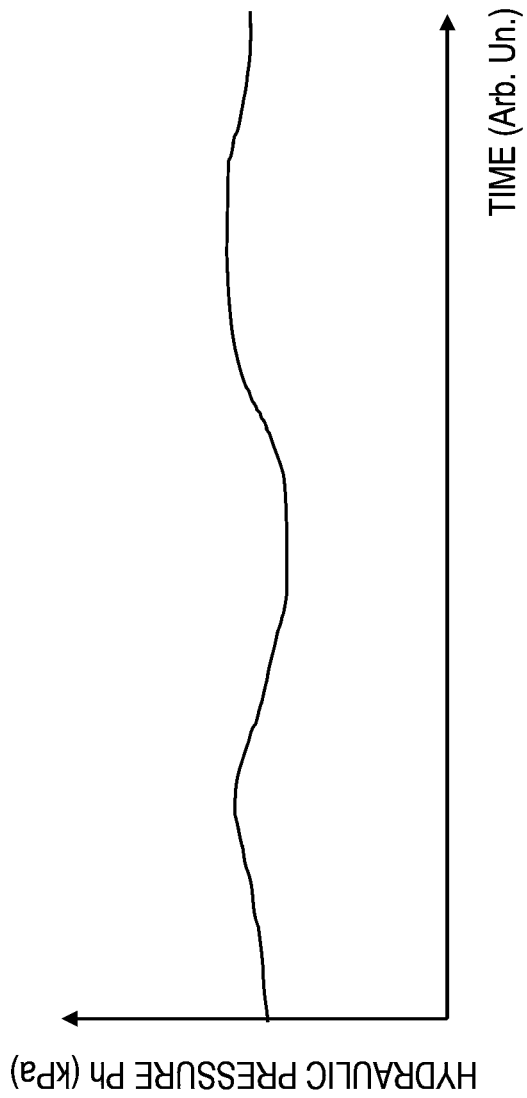
Fig. 14A
Fig. 14B

METHODS AND SYSTEMS FOR HANDLING FRESH CONCRETE BASED ON HYDRAULIC PRESSURE AND ON RHEOLOGICAL PROBE PRESSURE

CROSS REFERENCE TO RELATED APPLICATION

This application is 35 U.S.C. 371 National Phase Entry Application of PCT/US2019/017036, filed Feb. 7, 2019, which claims the benefit of U.S. Ser. No. 62/627,880 filed on Feb. 8, 2018, the disclosures of which are incorporated herein in their entirety by reference.

FIELD

The improvements generally relate to handling fresh concrete inside a rotating drum, and more particularly relate to such handling based on hydraulic pressure values indicative of pressure of a hydraulic fluid used for rotating the drum.

BACKGROUND

Fresh concrete is formed of a mixture of ingredients including at least cement-based material and water in given proportions. The ingredients are typically transported inside a drum of a mixer truck where the fresh concrete can be mixed prior to pouring thereof.

During handling of the fresh concrete, achieving and/or maintaining a satisfactory workability is a concern. It is commonplace in the field to obtain an indication of workability by performing a workability test. The workability can then be adjusted by adding water, aggregates and/or admixtures to the fresh concrete.

Some of these workability tests have been standardized such as the slump test JIS1100, the spread test DIN EN 12350, the slump flow tests ASTMC143 and BS EN12350. Generally, in these standard workability tests, a person is required to draw a sample of fresh concrete, manipulate it in a given way and deduce a workability value based on how the fresh concrete reacts to the manipulations.

Although such standard workability tests are satisfactory to a certain extent, there remains room for improvement.

SUMMARY

Workability determination techniques based on hydraulic pressure values have been discussed for many years such as in U.S. Pat. Nos. 4,900,154, 5,713,663 and 5,752,768. In these techniques, the workability of the fresh concrete is based on hydraulic pressure values indicative of pressure of a hydraulic fluid used for rotating the drum.

As can be understood, the torque required to rotate the drum depends on the workability of the fresh concrete inside the drum. For instance, fresh concrete of a higher workability may be stiffer, which may in turn require a higher torque for rotating the drum at a given rotation speed. Similarly, fresh concrete of a lower workability may be more fluid, which may require a lower torque for rotating the drum at the given rotation speed.

Accordingly, as the pressure of the hydraulic fluid used for rotating the drum is indicative of the torque required to rotate the drum, the workability of the fresh concrete can be determined based on the pressure of the hydraulic fluid and on some calibration data for the hydraulic pressure. However, the calibration data for the hydraulic pressure can vary over time, can vary as a function of a volume of fresh concrete inside the drum, can vary as a function of a rotation speed of the drum of the mixer truck and can be specific to each mixer truck. As such, these calibration data typically have to be determined frequently for each truck as a function of the volume of fresh concrete inside the drum. Such a calibration process has been found to be time and resource consuming in addition to the fact that manipulation errors could account for a substantial bias in the measured workability, especially when using the standard workability tests mentioned above.

The inventor found that rheological probes, such as the one described in International Patent Publication No. WO 2011/042880, can be used to determine the calibration data of an hydraulic pressure sensor in an efficient way. In one aspect, a probe pressure value indicative of pressure exerted on the rheological probe mounted inside the drum and immersed into the fresh concrete is received. A workability value indicative of the workability of the fresh concrete inside the drum is determined based on the probe pressure value and on calibration data for the rheological probe. A pressure value indicative of pressure of the hydraulic fluid used for rotating the drum is received and associated to the workability value to form the calibration data for the hydraulic pressure.

As can be understood, the calibration data for the rheological probe is less prone to variation than the calibration data for the hydraulic pressure as it is the same no matter in which truck it is installed and irrespective of the volume of fresh concrete inside the drum when a minimum volume is provided to submerge the rheological probe when at a bottom position inside the drum. Accordingly, it was found convenient to determine the calibration data for the hydraulic pressure based, at least on some extent, on the more trustable calibration data for the rheological probe.

These calibration steps can be performed for different operating conditions which can allow workability determination based on hydraulic pressure values for any one of the operating conditions included in the calibration data. Examples of operating conditions can include a volume of fresh concrete inside the drum, a rotation speed of the rotating drum, and the like.

It is contemplated that, during normal use of the mixer truck, the volume of fresh concrete inside the drum and/or the rotation speed of the drum will typically vary. Accordingly, in some embodiments, the calibration data for the hydraulic pressure are determined on the go during normal use of the mixer truck, which can reduce the time and resources usually attributed to determining such calibration data.

In accordance with one aspect, there is provided a method of determining calibration data for use in determining workability of fresh concrete inside a rotating drum based on hydraulic pressure, the method comprising the steps of: receiving a probe pressure value indicative of pressure exerted on a rheological probe mounted inside the drum and immerged in the fresh concrete; determining a workability value indicative of workability of the fresh concrete based on the probe pressure value and on calibration data for the rheological probe; receiving a hydraulic pressure value indicative of pressure of a hydraulic fluid used for rotating the drum; and determining hydraulic calibration data by associating the hydraulic pressure value and the workability value to one another.

In accordance with another aspect, there is provided a system comprising: a frame; a drum rotatably mounted to the frame for receiving fresh concrete; a driving device mounted to the frame for driving rotation of the drum using a hydraulic fluid; an hydraulic pressure sensor mounted to the driving device for measuring pressure of the hydraulic fluid; a rheological probe mounted inside the drum for measuring pressure exerted onto the rheological probe at least by resistance due to the movement of the rheological probe in the fresh concrete by rotation of the drum; and a controller communicatively coupled with the hydraulic pressure sensor and with the rheological probe, the controller being configured for performing the steps of: receiving a probe pressure value indicative of pressure exerted on the rheological probe; determining a workability value indicative of workability of the fresh concrete based on the probe pressure value and on calibration data for the rheological probe; receiving a hydraulic pressure value indicative of pressure of the hydraulic fluid; and determining hydraulic calibration data by associating the hydraulic pressure value and the workability value to one another.

In accordance with another aspect, there is provided a method of determining workability of fresh concrete inside a rotating drum, the method comprising: receiving a hydraulic pressure value indicative of pressure of a hydraulic fluid used for rotating the drum; and determining a workability value indicative of workability of the fresh concrete based on the received hydraulic pressure value and on the hydraulic calibration data as determined above.

In accordance with another aspect, there is provided a system comprising: a frame; a drum rotatably mounted to the frame for receiving fresh concrete; a driving device mounted to the frame for driving rotation of the drum using a hydraulic fluid; an hydraulic pressure sensor mounted to the driving device for measuring pressure of the hydraulic fluid; a controller communicatively coupled with the hydraulic pressure sensor and with the rheological probe, the controller having the hydraulic calibration data of claim 1 stored thereon, the controller being configured for performing the steps of: receiving a hydraulic pressure value indicative of pressure of a hydraulic fluid used for rotating the drum; and determining a workability value indicative of workability of the fresh concrete based on the received hydraulic pressure value and on the hydraulic calibration data as determined above.

In accordance with another aspect, there is provided a method of handling fresh concrete inside a rotating drum, the method comprising: receiving a probe pressure value indicative of pressure exerted on a rheological probe mounted inside the drum and immerged in the fresh concrete; receiving a hydraulic pressure value indicative of pressure of a hydraulic fluid used for rotating the drum; and handling the fresh concrete based on the probe pressure value, on the hydraulic pressure value and on corresponding calibration data.

In accordance with another aspect, there is provided a system comprising: a frame; a drum rotatably mounted to the frame for receiving fresh concrete; a driving device mounted to the frame for driving rotation of the drum using a hydraulic fluid; an hydraulic pressure sensor mounted to the driving device for measuring pressure of the hydraulic fluid; a rheological probe mounted inside the drum for measuring pressure exerted onto the rheological probe at least by resistance due to the movement of the rheological probe in the fresh concrete by rotation of the drum; and a controller communicatively coupled with the hydraulic pressure sensor and with the rheological probe, the controller being configured for performing the steps of: receiving a probe pressure value indicative of pressure exerted on a rheological probe mounted inside the drum and immerged in the fresh concrete; receiving a hydraulic pressure value indicative of pressure of a hydraulic fluid used for rotating the drum; and handling the fresh concrete based on the probe pressure value, on the hydraulic pressure value and on corresponding calibration data.

In accordance with another aspect, there is provided a method of determining workability of fresh concrete inside a rotating drum based on pressure, the method comprising: receiving an input concerning the fresh concrete inside the drum; receiving a probe pressure value indicative of pressure exerted on a rheological probe mounted inside the drum and immerged in the fresh concrete; receiving a hydraulic pressure value indicative of hydraulic pressure of a hydraulic fluid used for rotating the drum; and determining a workability value indicative of workability of the fresh concrete using one of the probe pressure value and the hydraulic pressure value based on the received input.

In accordance with another aspect, there is provided a system comprising: a frame; a drum rotatably mounted to the frame for receiving fresh concrete; a driving device mounted to the frame for driving rotation of the drum using a hydraulic fluid; an hydraulic pressure sensor mounted to the driving device for measuring pressure of the hydraulic fluid; a rheological probe mounted inside the drum for measuring pressure exerted onto the rheological probe at least by resistance due to the movement of the rheological probe in the fresh concrete by rotation of the drum; and a controller communicatively coupled with the hydraulic pressure sensor and with the rheological probe, the controller being configured for performing the steps of: receiving an input concerning the fresh concrete inside the drum; receiving a probe pressure value indicative of pressure exerted on a rheological probe mounted inside the drum and immerged in the fresh concrete; receiving a hydraulic pressure value indicative of hydraulic pressure of a hydraulic fluid used for rotating the drum; and determining a workability value indicative of workability of the fresh concrete using one of the probe pressure value and the hydraulic pressure value based on the received input.

It will be understood that the expression "computer" as used herein is not to be interpreted in a limiting manner. It is rather used in a broad sense to generally refer to the combination of some form of one or more processing units and some form of memory system accessible by the processing unit(s). Similarly, the expression "controller" as used herein is not to be interpreted in a limiting manner but rather in a general sense of a device, or of a system having more than one device, performing the function(s) of controlling one or more device such as an electronic device or a driving device for instance.

It will be understood that the various functions of a computer or of a controller can be performed by hardware or by a combination of both hardware and software. For example, hardware can include logic gates included as part of a silicon chip of the processor. Software can be in the form of data such as computer-readable instructions stored in the memory system. With respect to a computer, a controller, a processing unit, or a processor chip, the expression "configured to" relates to the presence of hardware or a combination of hardware and software which is operable to perform the associated functions.

Many further features and combinations thereof concerning the present improvements will appear to those skilled in the art following a reading of the instant disclosure.

DESCRIPTION OF THE FIGURES

In the figures,

FIGS. 9A and 9B are tables showing exemplary calibration data for the hydraulic pressure, for different volume values and different rotation speed values, in accordance with an embodiment;

FIG. 14A is a graph showing rotation speed values indicative of rotation speed of a rotating drum as a function of time, in accordance with an embodiment; and FIG. 14B is a graph showing hydraulic pressure values indicative of pressure of a hydraulic fluid used for rotating a drum as a function of time, in accordance with an embodiment.

DETAILED DESCRIPTION

Figure 1:
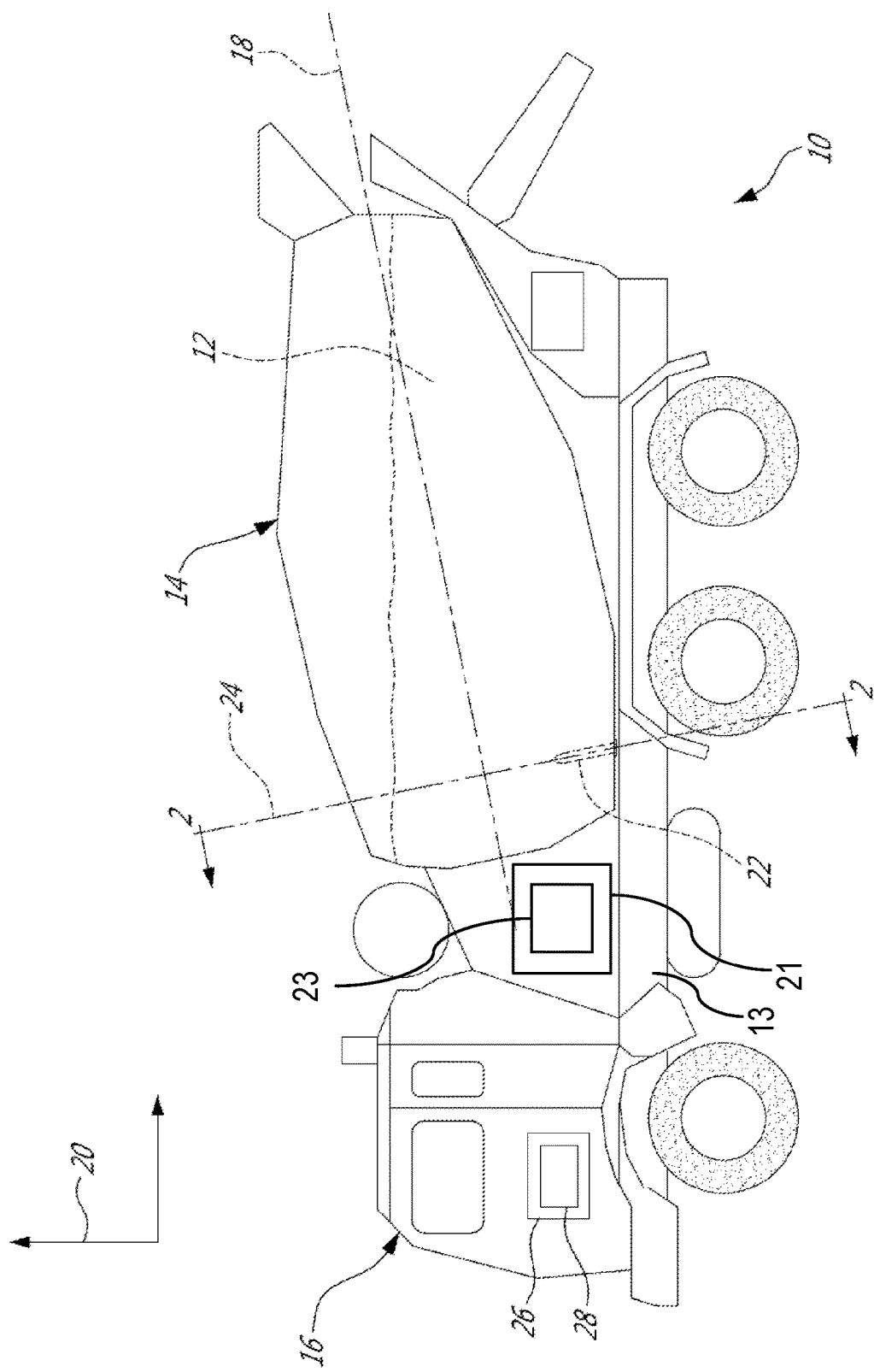
FIG. 1 is a side elevation view of an example of a system for handling fresh concrete inside a drum of a mixer truck, showing a controller, a rheological probe mounted inside the drum and a driving device for rotating the drum, in accordance with an embodiment.

FIG. 1 shows an example of a system 10 for handling fresh concrete 12. As shown, the system 10 has a frame 13 and a rotating drum 14 which is rotatably mounted to the frame 13. In this specific example, the frame 13 is part of a mixer truck 16. As such, the drum 14 can be rotated about a rotation axis 18 which is at least partially horizontally-oriented relative to the vertical 20.

The system 10 has a driving device 21 mounted to the frame 13 for driving rotation of the drum 14 using a hydraulic fluid. In this example, the hydraulic fluid can be oil (e.g., mineral oil), water and the like. A hydraulic pressure sensor 23 is mounted to the driving device 21 for measuring pressure of the hydraulic fluid as it is used to drive rotation of the drum 14.

As depicted, the system 10 has a rheological probe 22 mounted inside the drum 14 for measuring pressure exerted onto the rheological probe 22 at least by resistance due to the movement of the rheological probe 22 in the fresh concrete 12 by rotation of the drum 14.

Figure 2:
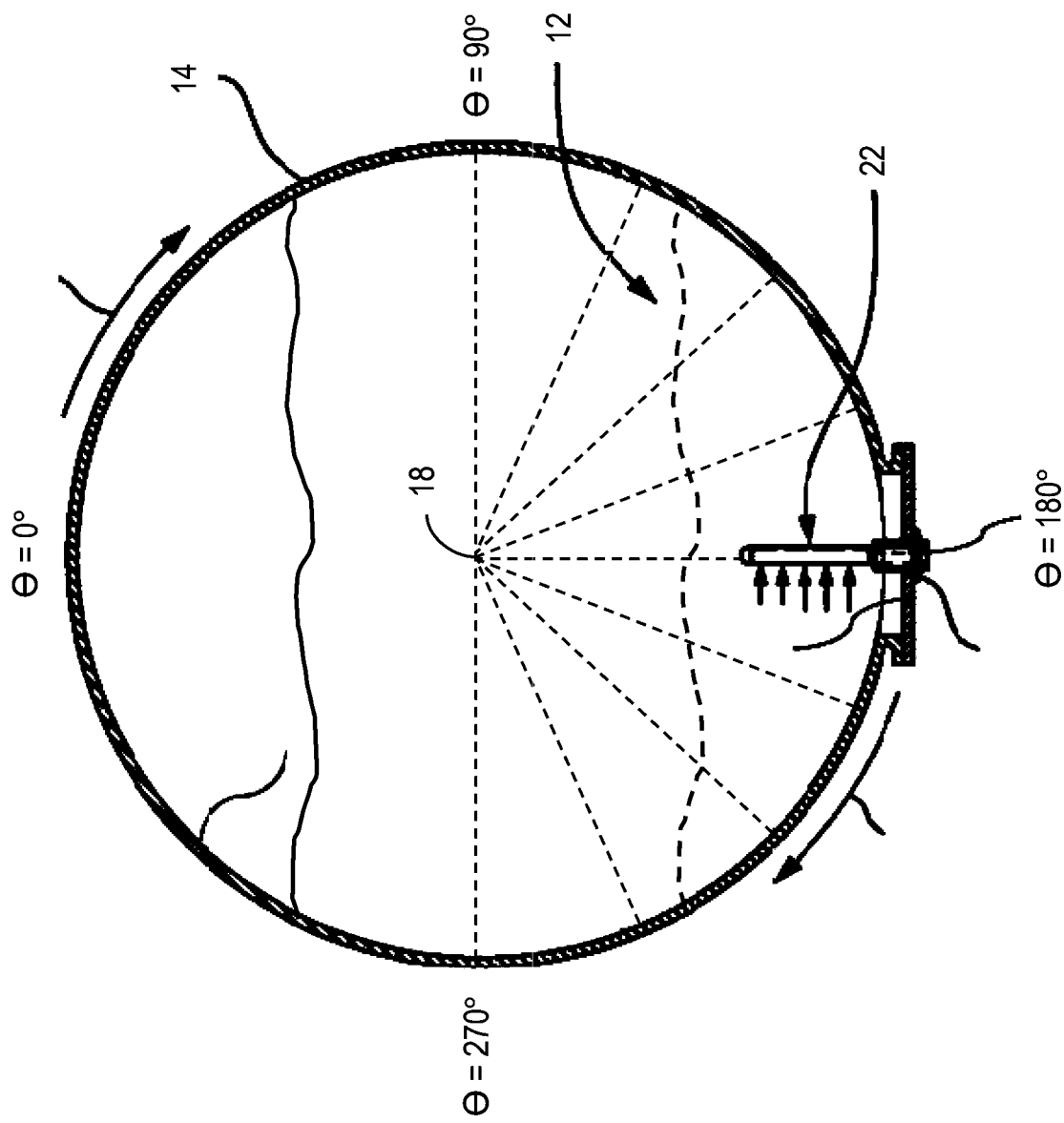
FIG. 2 is a sectional view taken along line 2-2 of FIG. 1.

As best seen in FIG. 2, the rheological probe 22 extends in a radial orientation 24 of the drum and reaches a plurality of circumferential positions ⊖ as the drum 14 rotates about the rotation axis 18. In this way, the rheological probe 22 can be used to measure probe pressure values as the rheological probe 22 is moved circumferentially in the fresh concrete 12 by the rotation of the drum 14 about the rotation axis 18.

More specifically, in this illustrated example, the rheological probe 22 is at a circumferential position ⊖ of 0° when at the top of the drum 14, at a circumferential position of 90° when at the right of the drum 14, at a circumferential position of 180° when at the bottom of the drum 14, and at a circumferential position of 270° when at the left of the drum 14. Such definition of the circumferential positions ⊖ is exemplary only as the circumferential positions ⊖ could have been defined otherwise depending on the embodiment.

A potential example of the rheological probe 22 is described in International Patent Publication No. WO 2011/042880.

Referring back to FIG. 1, the system 10 has a controller 26 which is communicatively coupled at least with the hydraulic pressure sensor 23 and with the rheological probe 22. The communication between the controller 26 and the driving device 21 can be provided by a wireless connection, a wired connection, or a combination thereof. Similarly, the communication between the controller 26 and the rheological probe 22 can be provided by a wireless connection, a wired connection, or a combination thereof.

In this specific embodiment, the system 10 has a user interface 28 which is communicatively coupled with the controller 26. As can be understood, the user interface 28 can be used to receive inputs and/or display data. Examples of inputs that can be received via the user interface 28 can include an indication of a viscosity (e.g., type of, viscosity value, viscosity range) of the fresh concrete 12 inside the drum 14, an indication of a volume of fresh concrete 12 inside the drum and/or an indication of a rotation speed of the drum 14. Examples of data that can be displayed by the user interface 28 can include pressure probe values received from the rheological probe 22, hydraulic pressure values received from the hydraulic sensor 23, and/or workability values indicative of the workability of the fresh concrete 12 inside the drum as determined using the methods described herein.

Figure 3:
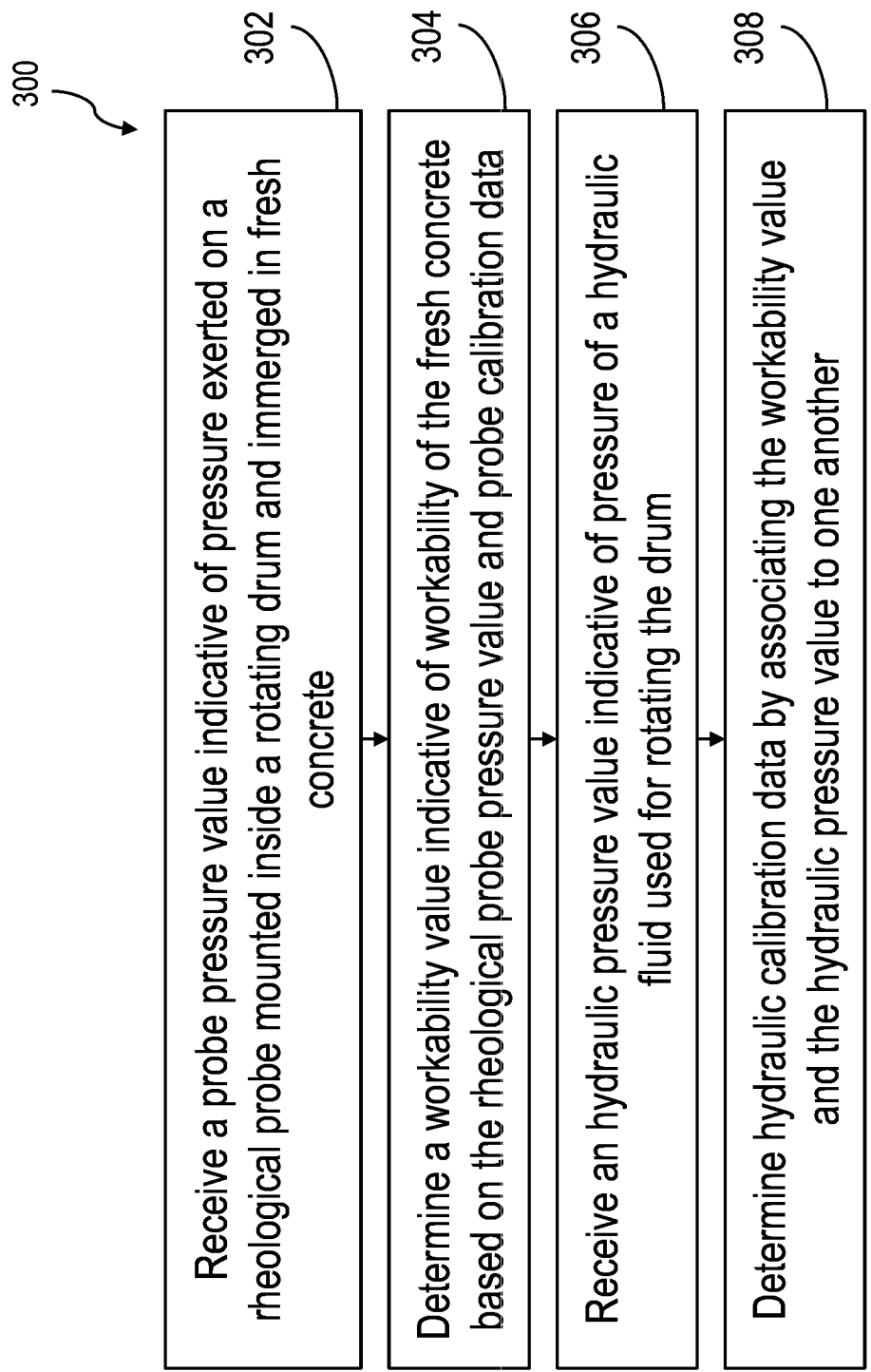
FIG. 3 is a flowchart of an example of a method for determining calibration data for use in determining workability of fresh concrete inside a rotating drum based on hydraulic pressure, in accordance with an embodiment.

FIG. 3 shows an example of a method 300 of determining calibration data for use in determining workability of the fresh concrete 12 inside the rotating drum 14 based on hydraulic pressure. As can be understood, the method 300 can be performed by the controller 26 and is described with reference to the system 10 of FIG. 1 for ease of reading.

At step 302, the controller 26 receives a first probe pressure value Pp1 indicative of pressure exerted on the rheological probe 22 mounted inside the drum 14 and immerged in the fresh concrete 12.

At step 304, the controller 26 determines a first workability value W1 indicative of workability of the fresh concrete 12 inside the drum 14 based on the first probe pressure value Pp1 and on calibration data for the rheological probe 22, conveniently referred to as probe calibration data (Ppi, Wi) herein.

At step 306, the controller 26 receives a first hydraulic pressure value Ph1 indicative of pressure of the hydraulic fluid used for rotating the drum 14 from the hydraulic pressure sensor 23.

At step 308, the controller 26 determines hydraulic sensor calibration data (Ph1, W1) by associating the first hydraulic pressure value Ph1 and the first workability value W1 to one another.

Figure 4:
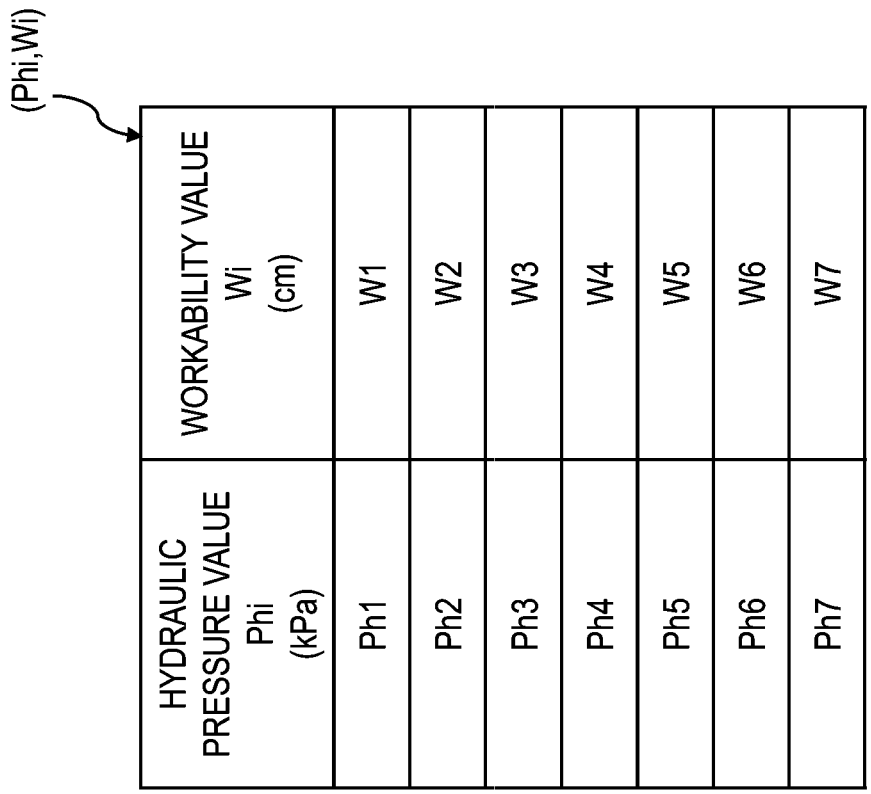
FIG. 4 is a table showing exemplary calibration data for the hydraulic pressure, in accordance with an embodiment.

In some embodiments, the steps 302, 304, 306 and 308 are repeated a number i of times, with i being an integer greater than the unity, when the drum 14 is loaded with fresh concrete of different workability values Wi so as to determine calibration data for the hydraulic pressure, conveniently referred to as hydraulic calibration data (Phi, Wi) herein. An example of the hydraulic calibration data (Phi, Wi) is shown in FIG. 4.

Accordingly, as can be understood, when the hydraulic calibration data (Phi, Wi) have been previously determined using the method 300, the workability value Wi of the fresh concrete 12 inside the drum 14 can be determined at least based on the hydraulic pressure value Phi received from the hydraulic pressure sensor 23. For instance, when a given hydraulic pressure Ph3, is received, the workability value can be determined to be the workability value W3 which is associated to the given hydraulic pressure Ph3 in the hydraulic calibration data (Phi, Wi), and so forth.

In some embodiments, the steps 302, 304, 306 and 308 are performed for given operating conditions A of the mixer truck 16, in which case hydraulic calibration data $(Phi, Wi)_A$ are determined by associating the workability value Wi, the hydraulic pressure value Phi and the given operating conditions A to one another.

The method 300 can also include a step of repeating the steps 302, 304, 306 and 308 for different operating conditions so as to determine hydraulic calibration data for each one of these different operating conditions. For instance, hydraulic calibration data $(Phi, Wi)_A$ can be determined when the steps 302, 304, 306 and 308 are performed for first operating conditions A, hydraulic calibration data $(Phi, Wi)_B$ can be determined when the steps 302, 304, 306 and 308 are performed for second operating conditions B, and so forth.

Accordingly, when the hydraulic calibration data $(Phi, Wi)_A$, $(Phi, Wi)_B$, etc. have been previously determined using the method 300, the workability value Wi of the fresh concrete 12 inside the drum 14 can be determined based on the hydraulic pressure value Phi received from the hydraulic pressure sensor 23 and on the operating conditions A, B, etc. as determined using the controller 26 and/or received using the user interface 28.

Examples of such operating conditions can include an indication of the viscosity of the fresh concrete inside the drum (e.g., normal fresh concrete, high strength fresh concrete, viscosity value or range), an indication of a volume of fresh concrete inside the drum 14 and/or an indication of a rotation speed at which the drum 14 is rotated. Other embodiments may apply.

As can be understood, the method 300 can be performed during normal use of the mixer truck 16. More specifically, the method 300 can be performed at given moments in time during normal use of the mixer truck 16. For instance, the method 300 can be performed after departing from a batching plant when the drum 14 is loaded with a given volume of fresh concrete, after discharging a given volume of the fresh concrete at a pour location, during mixing of the fresh concrete and the like. Performing the method 300 during normal use of the mixer truck 16 can allow to determine hydraulic calibration data for different operating conditions, which can later be used to determine workability based on hydraulic pressure values. In this way, determining the hydraulic calibration data associated to the mixer truck 16 may not necessarily require off time.

The controller 26 can be provided as a combination of hardware and software components. The hardware components can be implemented in the form of a computing device 500, an example of which is described with reference to FIG. 5. Moreover, the software components of the controller 26 can be implemented in the form of one or more software applications, examples of which are described with reference to FIGS. 6, 11 and 13.

Figure 5:
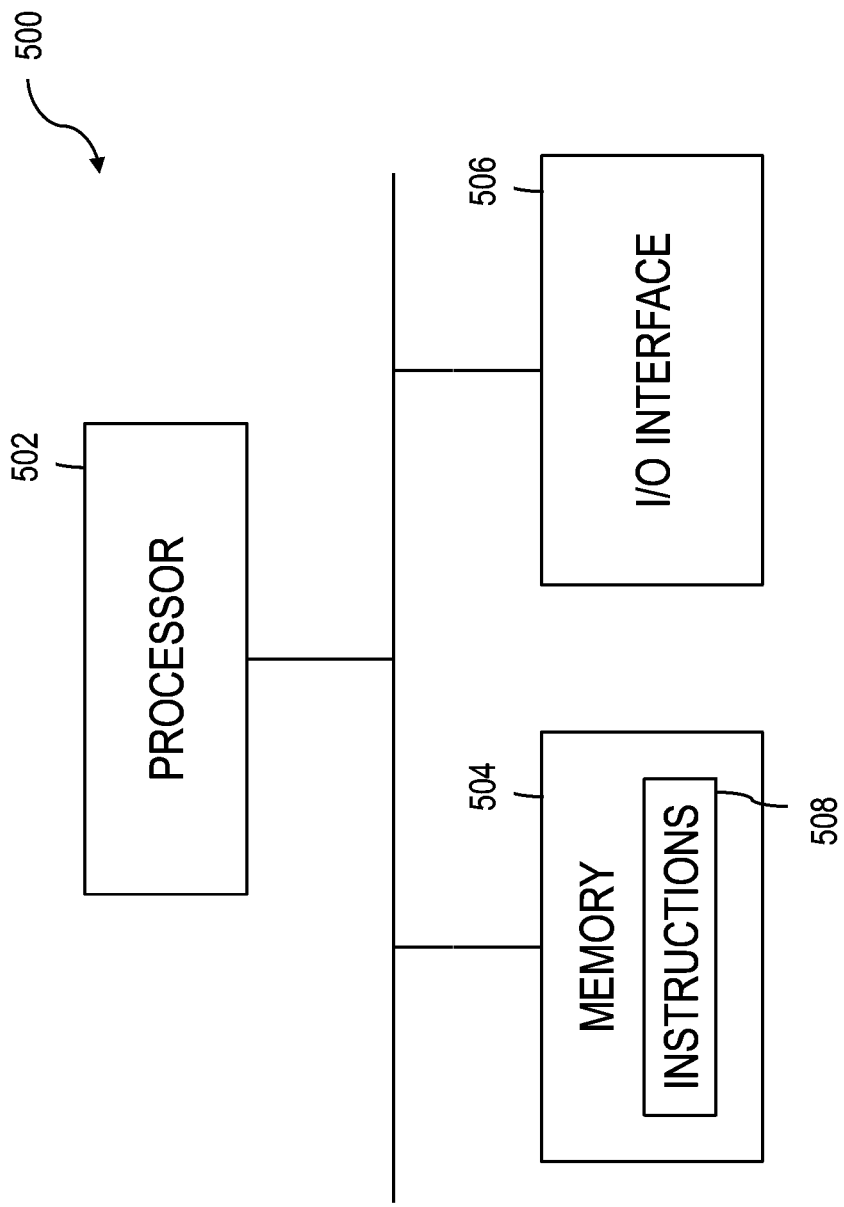
FIG. 5 is a schematic view of an example of a computing device of the controller of FIG. 1, in accordance with an embodiment.

Referring to FIG. 5, the computing device 500 can have a processor 502, a memory 504, and I/O interface 506. Instructions 508 for performing one or more computer-implemented methods, such as any of the methods described herein, can be stored on the memory 504 and accessible by the processor 502.

The processor 502 can be, for example, a general-purpose microprocessor or microcontroller, a digital signal processing (DSP) processor, an integrated circuit, a field programmable gate array (FPGA), a reconfigurable processor, a programmable read-only memory (PROM), or any combination thereof.

The memory 504 can include a suitable combination of any type of computer-readable memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface 506 enables the computing device 500 to interconnect with one or more input devices, such as the driving device 21, the hydraulic pressure sensor 23, the rheological probe 22 and/or the user interface 28, or with one or more output devices such as the driving device 21 and/or the user interface 28.

Each I/O interface 506 enables the computing device 500 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g., Wi-Fi, WiMAX), SS7 signaling network, fixed line, local area network, wide area network, and others, including any combination of these.

Figure 6:
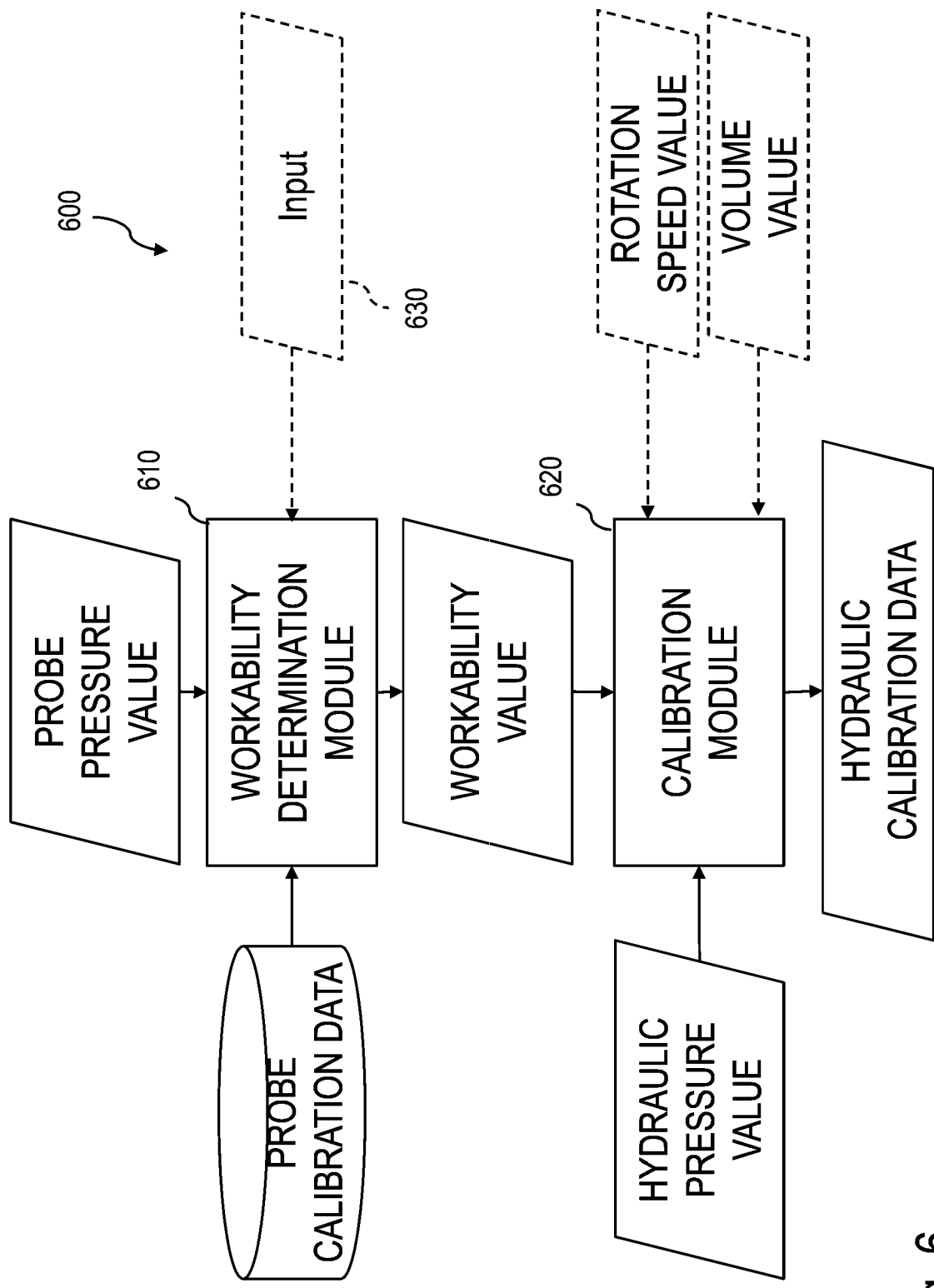
FIG. 6 is a schematic view of an example of a software application of the controller of FIG. 1 being configured to perform the method of FIG. 3, in accordance with an embodiment.

FIG. 6 shows an example of a software application 600 used to perform the method 300 of FIG. 3. As shown, the software application 600 includes a workability determination module 610 and a calibration module 620 communicatively coupled to one another.

As shown, the workability determination module 610 receives a first probe pressure value Pp1.

The first probe pressure value Pp1 can be received directly from the rheological probe 22. However, the first probe pressure value Pp1 can also result from processing of signal and/or data received from the rheological probe 22. An example of data received from the rheological probe 22 is shown in FIG. 7.

Figure 7:
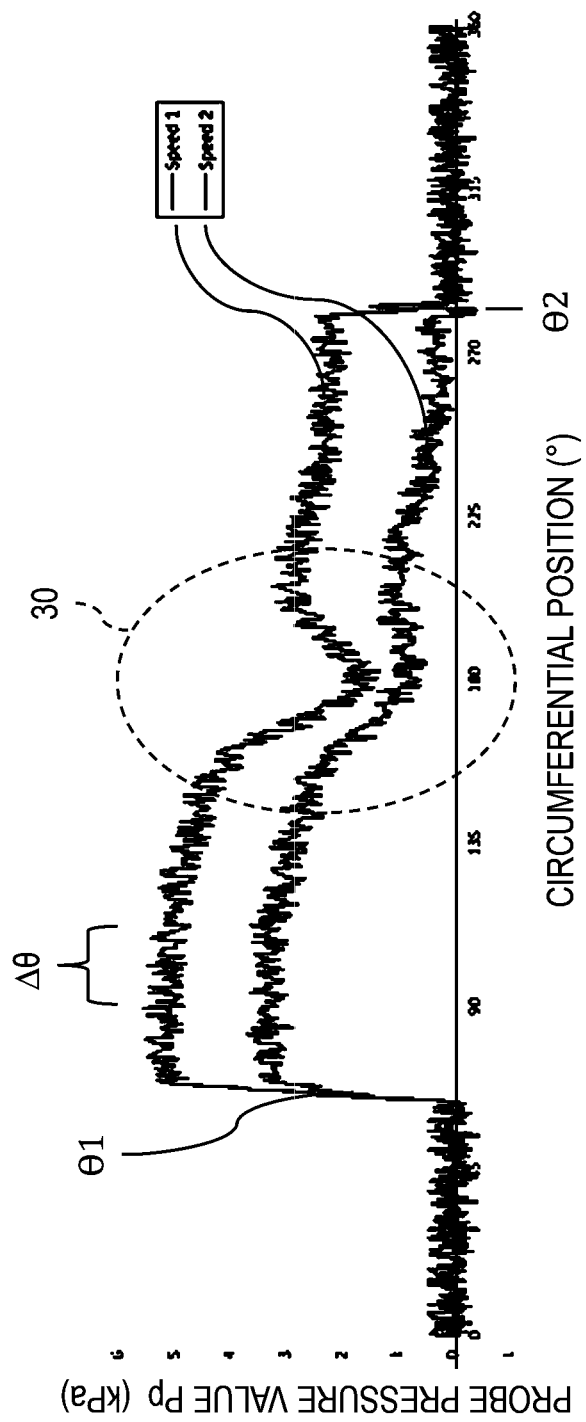
FIG. 7 is an example of a graph showing, for two different rotation speeds of a drum, experimental probe pressure values indicative of pressure exerted on the rheological probe of FIG. 1 by fresh concrete during a rotation of the drum, with discrepancies for probe pressure values measured in the vicinity of the bottom of the drum, in accordance with an embodiment.

More specifically, FIG. 7 shows an example of an experimental relationship between probe pressure values Pp as a function of its circumferential position when the rheological probe 22 is submerged into the fresh concrete 12 during a single rotation of the drum 14.

In some embodiments, the first probe pressure value Pp1 corresponds to one of the probe pressure values Pp associated to a given circumferential position $\ominus$. For instance, the first probe pressure value Pp1 received can correspond to the probe pressure value associated to the circumferential position $\ominus=90°$.

In some other embodiments, the first probe pressure value Pp1 corresponds to an average of the probe pressure values Pp of a given circumferential range $\Delta\ominus$. For instance, the first probe pressure value Pp1 can correspond to an average of the probe pressure values Pp ranging between $\ominus=90°$ and $\ominus=112.5°$.

As depicted, the probe pressure values Pp measured when the rheological probe 22 is in the vicinity of the bottom of the drum, i.e., near the circumferential position $\ominus=180°$, have some discrepancies 30 from what would be theoretically expected. These discrepancies 30 can stem from some movement of the fresh concrete along the rotation axis 18 of the drum 14 due to the mixing blade action which reduces the pressure on the rheological probe 22. Accordingly, the first probe pressure value Pp1 can be based on probe pressure value(s) measured when the rheological probe 22 is in the vicinity of the bottom of the drum 14 as it can allow a larger range of volume for which calibration data can be determined. In this case, the rheological probe 22 may be less affected by changes in the rotation speed of the drum 14. The first probe pressure value Pp1 can be based on probe pressure value(s) measured when the rheological probe 22 is at other circumferential positions in other embodiments.

In alternate embodiments, the first probe pressure value Pp1 can also stem from probe pressure values Pp taken during different rotations of the drum 14.

Referring back to FIG. 6, once the first probe pressure value Pp1 is received, the workability determination module 610 determines the first workability value W1 associated to the first probe pressure value Pp1 based on the probe calibration data (Ppi, Wi).

As can be understood, the probe calibration data (Ppi, Wi) are stored on a memory accessible by the controller 26. For instance, in some embodiments, the probe calibration data (Ppi, Wi) can be stored on the memory 504 of the computing device 500. In some other embodiments, the probe calibration data (Ppi, Wi) are stored on a remote memory which is accessible via a network such as the Internet, for instance.

Figures 8A, 8B:
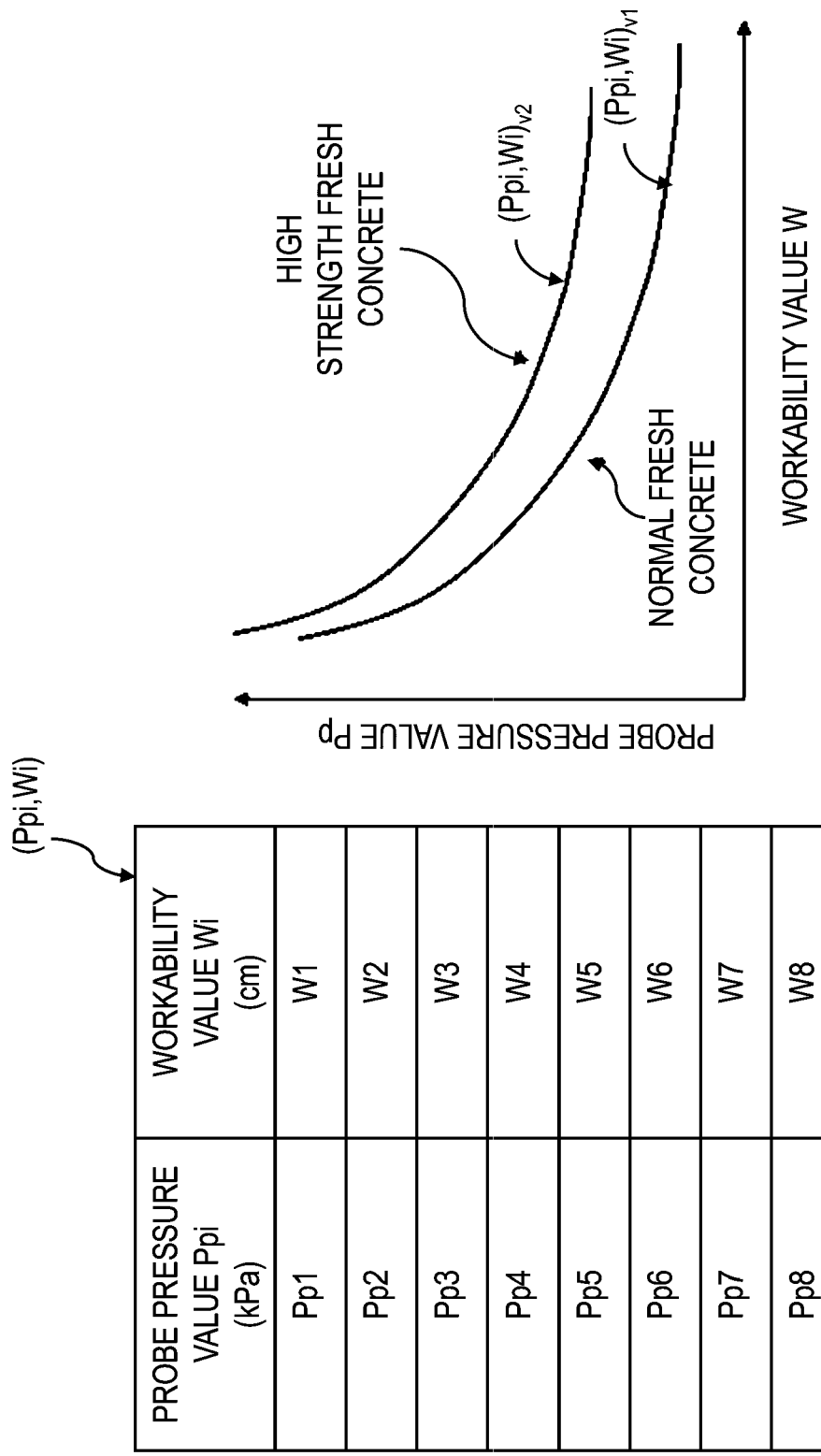
FIG. 8A is a table showing exemplary calibration data for the rheological probe of FIG. 1, in accordance with an embodiment.
FIG. 8B is a graph showing exemplary calibration data for the rheological probe of FIG. 1, for fresh concrete of different viscosities, in accordance with an embodiment.

An example of probe calibration data (Ppi, Wi) is shown in FIG. 8A. Although the illustrated probe calibration data (Ppi, Wi) are provided in the form of a lookup table, the probe calibration data (Ppi, Wi) can be provided in the form of a mathematical relation or any other suitable form.

The workability determination module 610 may have access to a number j of sets of probe calibration data (Ppi, Wi)$_j$ associated to different operating conditions, with j being an integer greater than the unity, examples of which are shown in FIG. 8B.

More specifically, FIG. 8B shows first and second probe calibration data (Ppi, Wi)$_{v1}$ and (Ppi, Wi)$_{v2}$ which are associated to different types of fresh concrete. For instance, in this example, the first probe calibration data (Ppi, Wi)$_{v1}$ are associated to a normal fresh concrete (i.e., fresh concrete having a normal viscosity v1) whereas the second probe calibration data (Ppi, Wi)$_{v2}$ are associated to high strength fresh concrete (i.e., fresh concrete having a higher than normal viscosity v2, with v2>v1).

As such, when it is determined that the fresh concrete 12 inside the drum 14 is a high strength fresh concrete, the workability determination module 610 can determine the first workability value W1 based on the probe calibration data (Ppi, Wi)$_{v2}$ rather than on the probe calibration data (Ppi, Wi)$_{v1}$, for instance.

Referring back to FIG. 6, the workability determination module 610 may receive an input 630 which indicates which one of the sets of probe calibration data (Ppi, Wi)$_j$ should be used in the determination of the first workability value W1. For instance, the received input 630 may be indicative that the fresh concrete 12 inside the drum 14 is a high strength fresh concrete, in which case the workability determination module 610 may select the second probe calibration data (Ppi, Wi)$_{v2}$ of FIG. 8B for the determination of the first workability value W1.

Once the first workability value W1 is determined, the workability determination module 610 communicates it to the calibration module 620.

As shown, the workability determination module 610 receives a first hydraulic pressure value Ph1.

The first hydraulic pressure value Ph1 can be received directly from the hydraulic pressure sensor 23. However, the first hydraulic pressure value Ph1 can also result from processing of signal and/or data received from the hydraulic pressure sensor 23.

Once the first workability value W1 and the first hydraulic probe pressure Ph1 are received, the calibration module 620 determines hydraulic calibration data (Ph1, W1) by associating the first hydraulic probe pressure Ph1 and the first workability value W1 to one another.

As mentioned above, hydraulic calibration data (Phi, Wi) such as shown in FIG. 4 can be determined by repeating the method 300 a number i of times when the drum 14 is loaded with fresh concrete of different workability values Wi.

Accordingly, as can be understood, when the hydraulic calibration data (Phi, Wi) have been so-determined, the workability value Wi of the fresh concrete 12 inside the drum 14 can be determined at least based on a hydraulic pressure value Phi received directly or indirectly from the hydraulic pressure sensor 23.

As mentioned above, hydraulic calibration data (Phi, Wi) can be determined for different operating conditions.

For instance, in some embodiments, the calibration module 620 can receive a rotation speed value Vri indicative of a rotation speed of the drum 14. In these embodiments, the calibration module 620 can determine hydraulic calibration data (Phi, Vri, Wi) by associating the hydraulic pressure value Phi, the rotation speed value Vri, and the workability value Wi to one another.

In some other embodiments, the calibration module 620 can receive a volume value Vi indicative of a volume of the fresh concrete 12 inside the drum 14. In these embodiments, the calibration module 620 can determine hydraulic calibration data (Phi, Vi, Wi) by associating the hydraulic pressure value Phi, the volume value Vi, and the workability value Wi to one another.

In alternate embodiments, the calibration module 620 can receive both a volume value Vi indicative of a volume of the fresh concrete 12 inside the drum 14 and a rotation speed value Vri indicative of a rotation speed of the drum 14. In such embodiments, the calibration module 620 can determine hydraulic calibration data (Phi, Vi, Vri, Wi) by associating the hydraulic pressure value Phi, the volume value Vi, the rotation speed value Vri, and the workability value Wi to one another. FIGS. 9A and 9B show an example of hydraulic calibration data (Phi, Vi, Vri, Wi) by way of hydraulic calibration data $(Phi, Vi, Wi)_{vr1}$ and $(Phi, Vi, Wi)_{vr2}$.

As can be understood, the rotation speed value Vri and/or the volume value Vi can be determined upon processing signal and/or data received from the rheological probe 22. For instance, referring back to the graph of FIG. 7, the volume value Vi can be determined based on a difference between a first circumferential position $\ominus 1$ at which the rheological probe enters in the fresh concrete 12 and a second circumferential position $\ominus 2$ at which the rheological probe 22 exits the fresh concrete 12.

Figure 10:
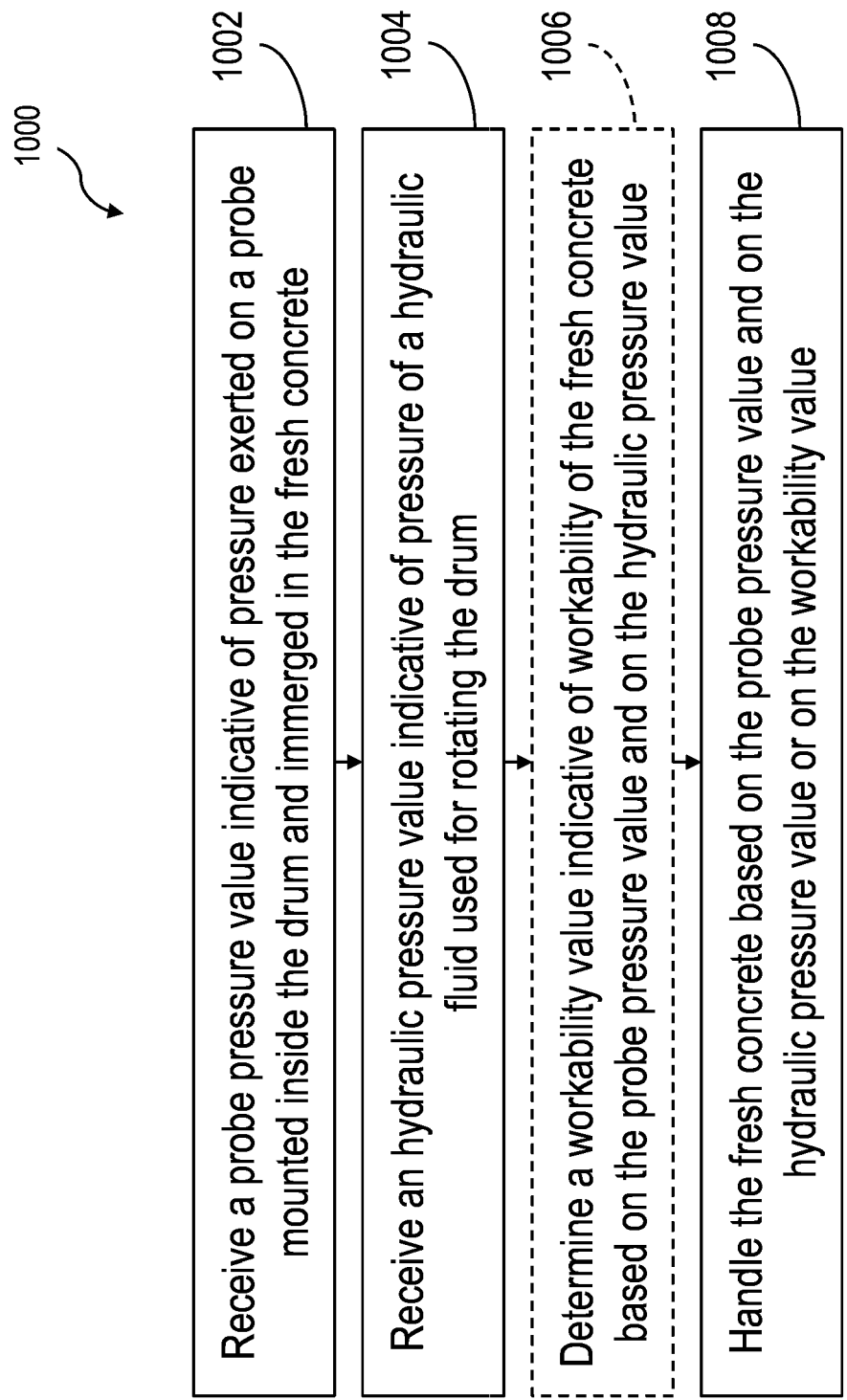
FIG. 10 is a flowchart of an example of a method of handling fresh concrete inside a rotating drum, in accordance with an embodiment.

FIG. 10 shows an example of a method 1000 for handling fresh concrete. As can be understood, the method 1000 can be performed by the controller 26 and is described with reference to the system 10 of FIG. 1 for ease of reading.

At step 1002, the controller 26 receives a probe pressure value Pp indicative of pressure exerted on the rheological probe 22 mounted inside the drum 14 and immerged in the fresh concrete 12.

At step 1004, the controller 26 receives a hydraulic pressure value Ph indicative of pressure of the hydraulic fluid used for rotating the drum 14.

In some embodiments, at step 1006, the controller 26 determines a workability value W indicative of workability of the fresh concrete 12 based on the probe pressure value Pp and on the hydraulic pressure value Ph.

At step 1008, the controller 26 handles the fresh concrete 12 based on the probe pressure value Pp and on the hydraulic pressure value Ph or optionally on the workability value W.

For instance, the fresh concrete 12 can be handled by adding ingredients to the fresh concrete 12, by maintaining mixing of the fresh concrete 12 and/or by pouring the fresh concrete 12.

Figure 11:
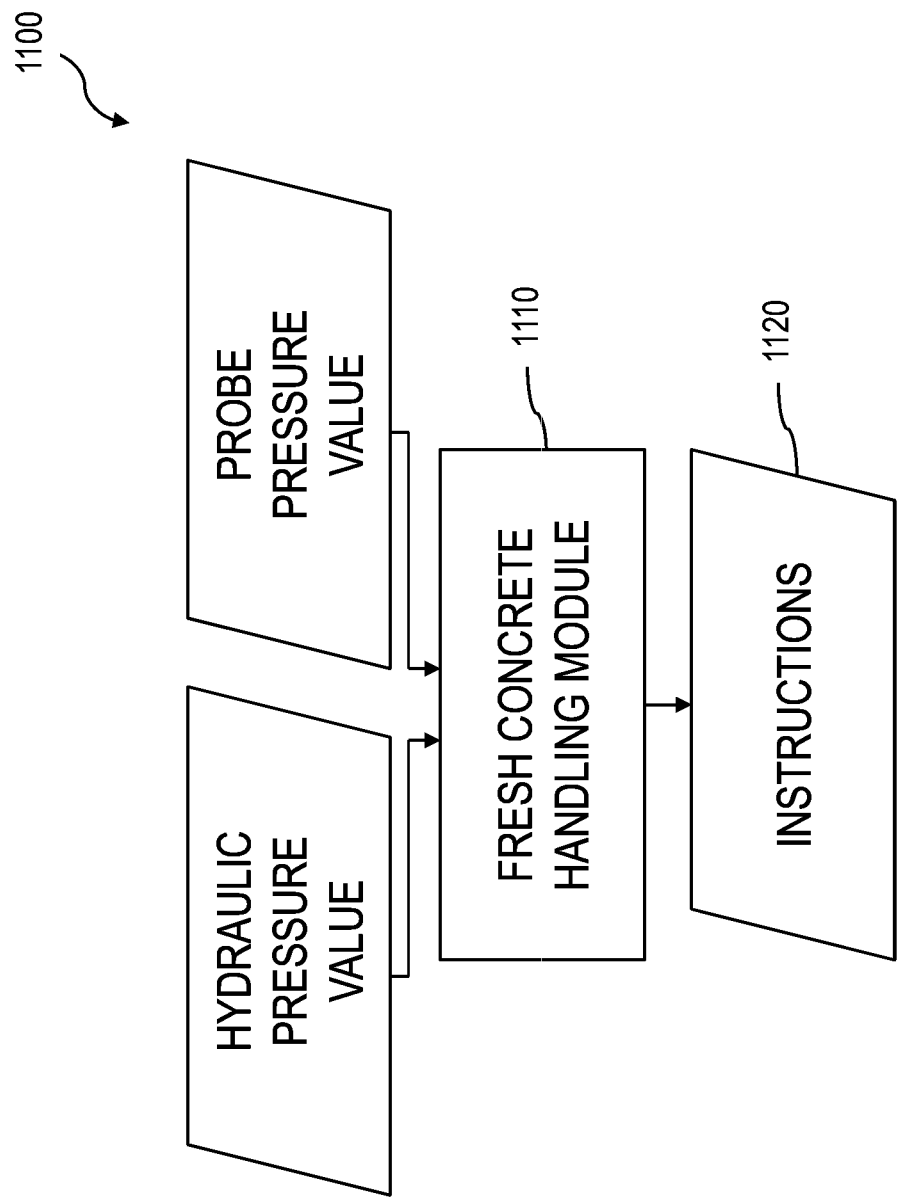
FIG. 11 is a schematic view of an example of a software application of the controller of FIG. 1 being configured to perform the method of FIG. 10, in accordance with an embodiment.

FIG. 11 shows an example of a software application 1100 used to perform the method 1000 of FIG. 10. As shown, the software application 1100 includes a fresh concrete handling module 1110.

The fresh concrete handling module 1110 receives a hydraulic pressure value Ph and a probe pressure value Pp and determines instructions 1120 to handle the fresh concrete 12 inside the drum 14 based on the received hydraulic pressure value Ph and on the received probe pressure value Pp.

In some embodiments, the fresh concrete handling module 1110 includes a workability determination module which is configured to determine a workability value W of the fresh concrete 12 inside the drum 14 based on the hydraulic pressure value Ph and on the probe pressure value Pp. In these embodiments, the workability value can be determined using either one or both of the probe calibration data (Ppi, Wi) and the hydraulic calibration data (Phi, Wi).

In alternate embodiments, the fresh concrete handling module 1110 may generate an alert when a first workability value determined using the probe pressure value Pp and the probe calibration data (Ppi, Wi) differs from a second workability value determined using the hydraulic pressure value Ph and the hydraulic calibration data (Pph, Wi) by more than a tolerance value.

Figure 12:
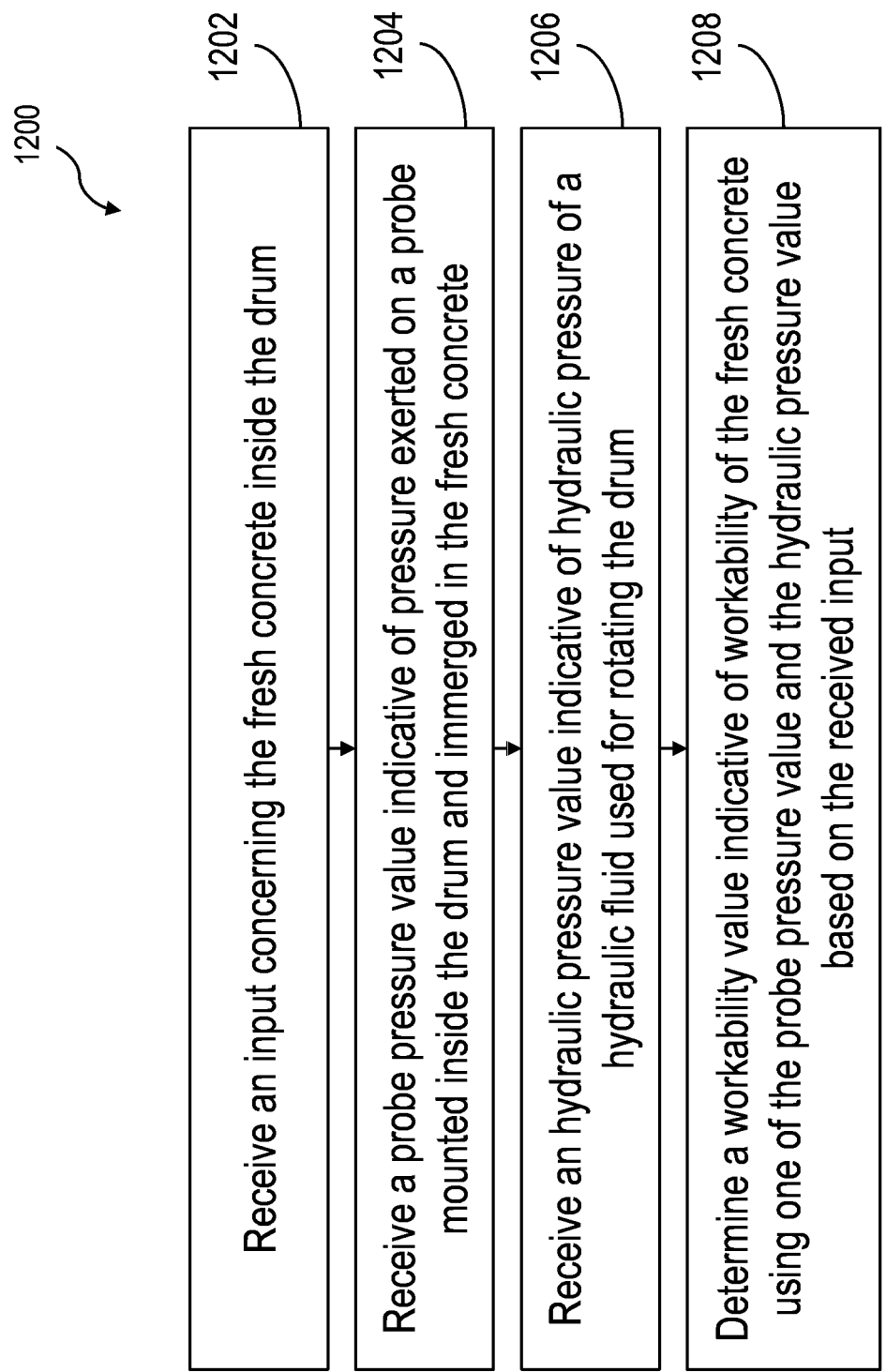
FIG. 12 is a flowchart of a method of determining workability of fresh concrete inside a rotating drum based either hydraulic pressure or probe pressure, in accordance with an embodiment.

FIG. 12 shows an example of a method 1200 for handling fresh concrete. As can be understood, the method 1200 can be performed by the controller 26 and is described with reference to the system 10 of FIG. 1 for ease of reading.

At step 1202, the controller 26 receives an input concerning the fresh concrete 12 inside the drum 14. The input can be received via the rheological probe 22, the hydraulic pressure sensor 23 and/or the user interface 28.

At step 1204, the controller 26 receives a probe pressure value Pp indicative of pressure exerted on the rheological probe 22 mounted inside the drum 14 and immerged in the fresh concrete 12.

At step 1206, the controller 26 receives a hydraulic pressure value indicative of hydraulic pressure of the hydraulic fluid used for rotating the drum 14.

At step 1208, the controller 26 determines a workability value indicative of workability of the fresh concrete 12 using one of the probe pressure value Pp and the hydraulic pressure value Ph based on the received input.

Figure 13:
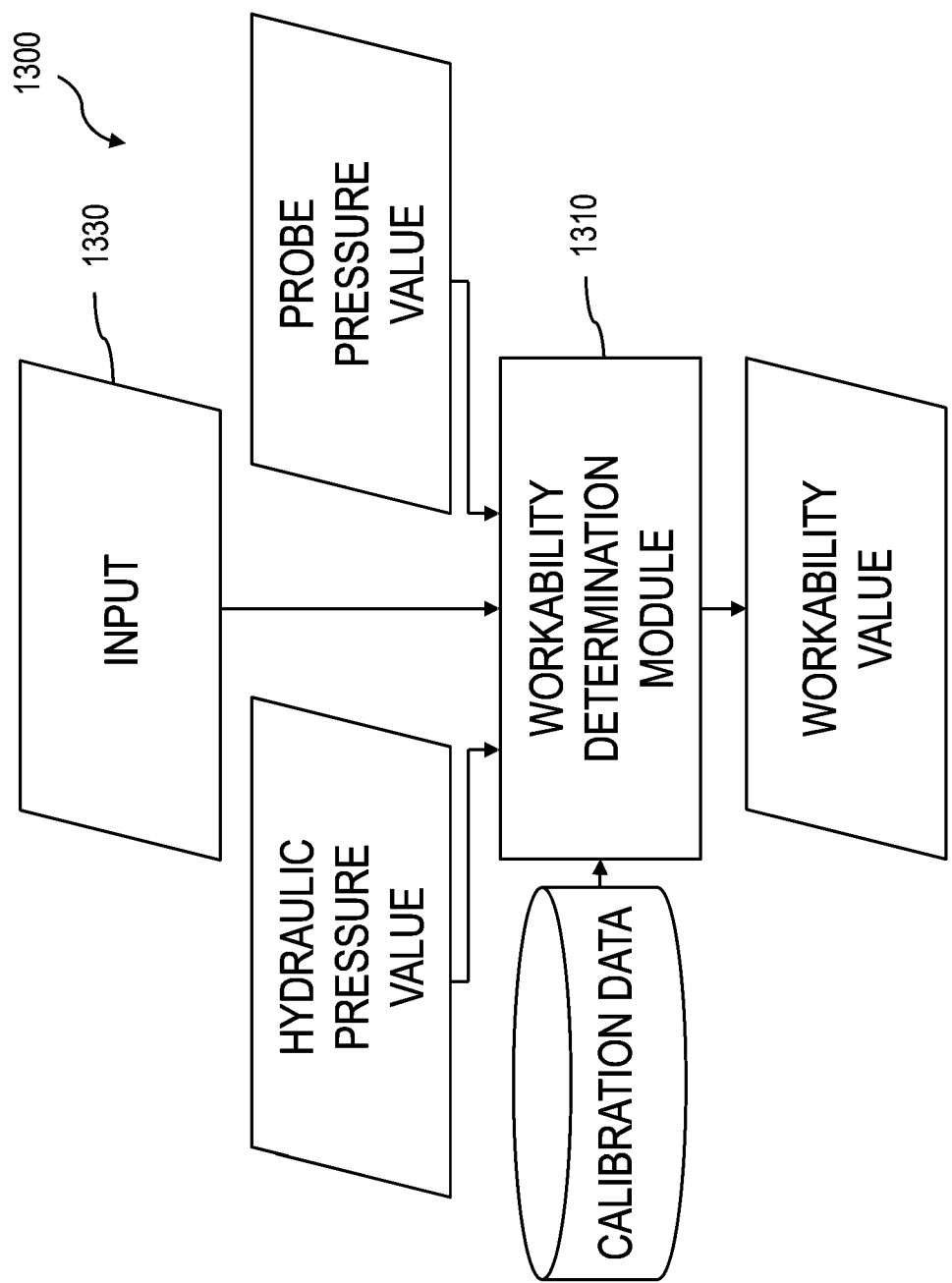
FIG. 13 is a schematic view of another example of a software application of the controller of FIG. 1 being configured to perform the method of FIG. 12, in accordance with an embodiment.

FIG. 13 shows an example of a software application 1300 used to perform the method 1200 of FIG. 12. As shown, the software application 1300 includes a workability determination module 1310.

As shown, the workability determination module 1310 receives an input 1330, a hydraulic pressure value Ph and a probe pressure value Pp.

Depending on the input 1330, the workability determination module 1310 is configured to determine a workability value W based either on the probe pressure value Pp or the hydraulic pressure value Ph, and the corresponding calibration data.

In some other embodiments, the input 1330 is indicative of rotation speed data indicative of a rotation speed of the drum 14 over time. In these embodiments, the workability determination module 1310 determines the workability value W using the hydraulic pressure value Ph and the corresponding calibration data (Phi, Wi) upon detecting a sudden change during a single rotation of the drum 14 in the rotation speed data. Such sudden changes in the rotation speed data are shown at 1400 in FIG. 14A, for instance. Such a sudden change can be a sudden increase and/or a sudden decrease of the rotation speed of the drum 14.

In these embodiments, the fact that there are one or more sudden changes of the rotation speed of the drum 14 is indicative that the fresh concrete 12 has a low viscosity in which case the workability value W can be best determined using the hydraulic pressure value Ph and the hydraulic calibration data (Phi, Wi).

Such sudden variations of the rotation speed of the drum 14 can result from the fresh concrete being so stiff that some portions thereof stick on the inner wall of the drum as it rotates, which causes these portions to be carried upwards and to then fall back towards the bottom of the drum, which can cause the rotation speed of the drum to suddenly vary.

In some embodiments, the input 1330 is indicative of a viscosity value v of the fresh concrete 12 inside the drum. In these embodiments, the workability determination module 1310 determines the workability value W using the hydraulic pressure value Ph and the corresponding calibration data (Phi, Wi) when the viscosity value v of the fresh concrete 12 exceeds a viscosity threshold value vth.

In alternate embodiments, the input 1330 is indicative of hydraulic pressure data indicative of the hydraulic pressure of the hydraulic fluid over time. In these embodiments, the workability determination module 1310 determines the workability value W using the probe pressure value Pp and the corresponding calibration data (Ppi, Wi) when the when the hydraulic pressure data vary smoothly. In these embodiments, using the probe pressure value Pp and the corresponding calibration data (Ppi, Wi) can provide more precision as the rheological probe 22 is generally more precise than the hydraulic pressure sensor 23. An example of a smooth hydraulic pressure variation is shown at FIG. 14B.

As can be understood, the examples described above and illustrated are intended to be exemplary only. For instance, the drum does not need to be rotatably mounted to a mixer truck. For instance, the drum can be part of a stationary concrete mixer such as those provided in concrete production plants. In some alternate embodiments, the rheological probe can be any type of internal probe, i.e., any probe which is mounted inside the drum. The scope is indicated by the appended claims.

What is claimed is:

1. A method of determining calibration data for use in determining workability of fresh concrete inside a rotating drum based on hydraulic pressure and handling the fresh concrete, the method comprising the steps of:
   receiving a probe pressure value indicative of pressure exerted on a rheological probe mounted inside the drum and immerged in the fresh concrete;
   determining a workability value indicative of workability of the fresh concrete based on the probe pressure value and on probe calibration data;
   receiving a hydraulic pressure value indicative of pressure of a hydraulic fluid used for rotating the drum; containing the given one of the fresh concrete samples;
   determining hydraulic calibration data by associating the hydraulic pressure value and the workability value to one another; and
   wherein, upon receiving a given hydraulic pressure value indicative of pressure of the hydraulic fluid used for rotating the drum containing the fresh concrete batch, associating a workability value to the fresh concrete batch using on the hydraulic calibration data and handling the fresh concrete batch based on the workability value.

2. The method of claim 1 wherein said steps of receiving the probe pressure value, determining the workability value, and receiving the hydraulic pressure value are performed for given operating conditions, said determining including determining the hydraulic calibration data by associating the hydraulic pressure value, the workability value and the given operating conditions to one another.

3. The method of claim 2 further comprising repeating the steps of receiving the probe pressure value, determining the workability value, receiving the hydraulic pressure value, and determining the hydraulic calibration data for different operating conditions.

4. The method of claim 2 wherein said given operating conditions include a volume value indicative of a volume of the fresh concrete inside the drum.

5. The method of claim 4 further comprising receiving a volume value indicative of a volume of the fresh concrete inside the drum, said determining the hydraulic calibration data including associating the hydraulic pressure value, the volume value and the workability value to one another.

6. The method of claim 2 wherein said operating conditions include a rotation speed value indicative of a rotation speed of the rotating drum.

7. The method of claim 6 further comprising receiving a rotation speed value indicative of a rotation speed of the rotating drum, said determining the hydraulic calibration data including associating the hydraulic pressure value, the rotation speed value and the workability value to one another.

8. The method of claim 2, wherein the step of receiving the probe pressure value, determining the workability value and receiving the hydraulic pressure value are performed in a first operating condition, and further comprising, prior to the handling of the fresh concrete, the steps of:
   receiving a second probe pressure value indicative of the pressure exerted on the rheological probe mounted inside the drum and immerged in the fresh concrete in a second operating condition;
   determining a second workability value indicative of the workability of the fresh concrete based on the second probe pressure value and on the probe calibration data for the second operating condition;
   receiving a second hydraulic pressure value indicative of the pressure of the hydraulic fluid used for rotating the drum in the second operating condition; and
   determining further hydraulic calibration data by associating the second hydraulic pressure value and the second workability value to one another.

9. The method of claim 1 wherein the rotating drum is rotatably mounted to a mixer truck, the method being performed during normal use of the mixer truck.

10. A system comprising:
    a frame;
    a drum rotatably mounted to the frame for receiving a fresh concrete batch;
    a driving device mounted to the frame for driving rotation of the drum using a hydraulic fluid;
    an hydraulic pressure sensor mounted to the driving device for measuring pressure of the hydraulic fluid;
    a rheological probe mounted inside the drum for measuring pressure exerted onto the rheological probe at least by resistance due to the movement of the rheological probe in the fresh concrete batch by rotation of the drum; and
    a controller communicatively coupled with the hydraulic pressure sensor and with the rheological probe, the controller being configured for performing the steps of:
       performing a calibration sequence for different fresh concrete samples having different workabilities, each calibration sequence including:
       receiving a probe pressure value indicative of pressure exerted on the rheological probe;
       determining a workability value indicative of workability of the fresh concrete based on the probe pressure value and on calibration data for the rheological probe;
       receiving a hydraulic pressure value indicative of pressure of the hydraulic fluid; and
       determining hydraulic calibration data by associating the hydraulic pressure value and the workability value to one another; and
       wherein, upon receiving a given hydraulic pressure value indicative of pressure of the hydraulic fluid used for rotating the drum containing the fresh concrete batch, associating a workability value to the fresh concrete batch using on the hydraulic calibration data and providing instructions to handle the fresh concrete batch.

11. The system of claim 10 wherein said steps of receiving the probe pressure value, determining the workability value, and receiving the hydraulic pressure value are performed for given operating conditions, said determining including determining the hydraulic calibration data by associating the hydraulic pressure value, the workability value and the given operating conditions to one another.

12. The system of claim 11 wherein the controller is configured for repeating the steps of receiving the probe pressure value, determining the workability value, receiving the hydraulic pressure value, and determining the hydraulic calibration data for different operating conditions.

13. The system of claim 11 wherein said given operating conditions include a volume value indicative of a volume of the fresh concrete inside the drum.

14. The system of claim 13 wherein the controller is configured for receiving a volume value indicative of a volume of the fresh concrete inside the drum, said determining the hydraulic calibration data including associating the hydraulic pressure value, the workability value and the volume value to one another.

15. The system of claim 11 wherein said operating conditions include a rotation speed value indicative of a rotation speed of the rotating drum.

16. The system of claim 15 wherein the controller is configured for receiving a rotation speed value indicative of a rotation speed of the rotating drum, said determining the hydraulic calibration data including associating the hydraulic pressure value, the workability value and the rotation speed value to one another.

17. The system of claim 10 wherein the rotating drum is rotatably mounted to a mixer truck.

18. A method of handling fresh concrete inside a rotating drum, the method comprising:
  receiving a probe pressure value indicative of pressure exerted on a rheological probe mounted inside the drum and immerged in the fresh concrete;
  determining a first workability value indicative of workability of the fresh concrete based on the probe pressure value and on probe calibration data;
  receiving a hydraulic pressure value indicative of pressure of a hydraulic fluid used for rotating the drum;
  determining a second workability value indicative of the workability of fresh concrete based on the hydraulic pressure value and on hydraulic calibration data;
  handling the fresh concrete based on the second workability value contingent on the first workability value corresponding to the second workability value within a tolerance range.

19. The method of claim 18 wherein said handling the fresh concrete includes adding ingredients to the fresh concrete.

20. The method of claim 18 wherein said handling the fresh concrete includes pouring the fresh concrete.

* * * * *